United States Patent [19]

Hideshima et al.

[11] Patent Number: 4,968,130

[45] Date of Patent: Nov. 6, 1990

[54] LASER BEAM SCANNING TYPE OPHTHALMOLOGICAL INSTRUMENT

[75] Inventors: Masayuki Hideshima; Shinji Wada; Akihiko Sekine; Takashi Yokokura, all of Tokyo, Japan

[73] Assignee: Kabushiki Kaisha Topcon, Japan

[21] Appl. No.: 262,640

[22] Filed: Oct. 26, 1988

[30] Foreign Application Priority Data

Oct. 28, 1987 [JP] Japan .................................. 62-272097

[51] Int. Cl.$^5$ ............................ A61B 3/10; A61B 3/14
[52] U.S. Cl. ..................................... 351/221; 351/206
[58] Field of Search ........................ 351/205, 206, 221; 606/4, 5, 6; 354/62

[56] References Cited

U.S. PATENT DOCUMENTS 4,579,430 4/1986 Bille .................................... 351/206

Primary Examiner—Rodney B. Bovernick
Attorney, Agent, or Firm—Finnegan, Henderson, Farabow, Garrett & Dunner

[57] ABSTRACT

A laser beam scanning type ophthalmological instrument has a first laser beam light source for emitting a first laser beam; a second laser beam light source for emitting a second laser beam of a different wavelength from that of the first laser beam; and a light receiving element for receiving a laser beam reflected by an eye fundus, and in which the eye fundus is scanned by the first and second laser beams in order to observe the eye fundus or in order that a view field, etc. can be inspected. The laser beam scanning type ophthalmological instrument is characterized in that the first and second laser beams emitted by the first and second laser beam light sources can independently be adjusted in light quantity.

11 Claims, 3 Drawing Sheets

LASER BEAM SCANNING TYPE OPHTHALMOLOGICAL INSTRUMENT

BACKGROUND OF THE INVENTION

1. Field of the Invention

This invention relates to a laser beam scanning type ophthalmological instrument for scanning an eye fundus by laser beam coming from a laser beam light source in order to observe the eye fundus and to inspect the view field, etc.

2. Prior Art

A conventional laser beam scanning type ophthalmological instrument is used as an eye fundus camera in which a visible laser beam is emitted by a laser beam light source, an eye fundus is scanned by the visible laser beam, a reflecting light reflected on the eye fundus is received by a light receiving system and the eye fundus is displayed on a display screen according to the light received by the light receiving system so that the eye fundus can be observed, or as a subjective optometer in which projection of a laser beam is stopped for a scanning period of time in a desired position of the eye fundus and a target mark such as a landolt ring is formed in that position.

In the conventional laser beam scanning type ophthalmological instrument, however, since a laser beam for scanning the eye fundus is a visible light, the intensity of the laser beam is adjusted as weak as possible in order not to give an unpleasant feeling such as a dazzling to a person to be tested. Because of the foregoing adjustment, a sufficient reflecting light quantity is unobtainable when the reflectance is low at the eye fundus. This naturally makes it very difficult to observe the eye fundus. In order to avoid this undesirable problem to occur, there has been proposed a device, as disclosed for example in Japanese Pat. Early Laid-open Publication No. Sho 62-117524, in which an invisible light is utilized in order to render a certain quantity of background illumination or auxiliary illumination.

However, since the light quantity of the auxiliary illumination is constant in the above device, sometimes a satisfactory eye fundus image is unobtainable depending on conditions of the quantity of light which is used for stimulating the eye fundus for example, because there occurs a partial saturation and/or a shortage of light quantity.

SUMMARY OF THE INVENTION

A first object of the present invention is to provide a laser beam scanning type ophthalmological instrument, in which a satisfactory eye fundus image can always be obtained irrespective of the reflectance at the eye fundus.

A second object of the present invention is to provide a laser beam scanning type ophthalmological instrument, in which an eye fundus image of a predetermined brightness can be obtained irrespective of the reflectance at the eye fundus.

A third object of the present invention is to provide a laser beam scanning type ophthalmological instrument, in which when a place for stimulation or coagulation is designated, the designated place can be displayed on a display.

The feature of the present invention is that a first and a second laser beam light source are independently adjustable in light quantity.

Another feature of the present invention is that there is included a control means in which when a target value of output from a light receiving element and either one of a first and a second laser beams are established, the light quantity of the other laser beam can be established.

A further feature of the present invention is that there are included control means for separately controlling a first and a second laser beams which are emitted by a first and a second laser beam light source, and designating means for designating a desired position at an eye fundus, the control means modulating either one of a first and a second laser beams and displaying the designated position on a display.

DETAILED DESCRIPTION OF THE EMBODIMENTS

The embodiments of the present invention will be described with reference to the accompanying drawings.

Figure 1:
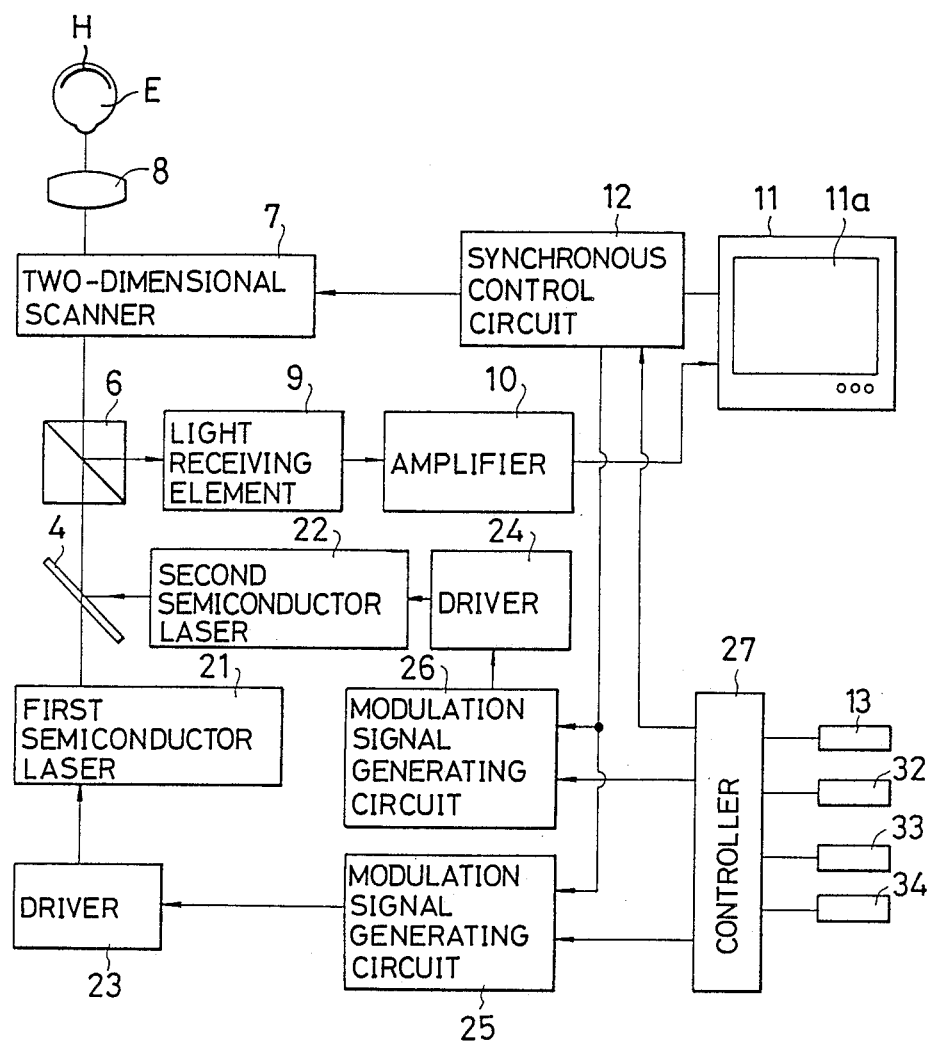
FIG. 1 is a block diagram schematically showing a laser beam scanning type ophthalmological instrument according to the present invention.
Figure 2:
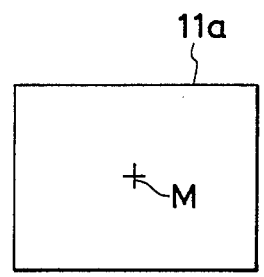
FIG. 2 is a schematic view of a display screen.

FIG. 1 is a block diagram schematically showing a laser beam scanning ophthalmological instrument according to the present invention. In the figure, 21 and 22 denote a first and a second semiconductor lasers for projecting a visible laser beam (first laser beam) and an infrared laser beam (second laser beam), 23 and 24 denote drivers for feeding an injection current to the first and the second semiconductor lasers 21 and 22 (first and second laser beam light sources) and for driving the semiconductor lasers 21 and 22, 25 and 26 denote a first and a second modulation signal generating circuits for outputting a first and a second modulation signals and controlling injection current, which is output by the drivers 23 and 24, to control the light quantity of the laser beams, and 27 denotes a controller for controlling the output timing of modulation signals, which are output by the first and the second modulation signal generating circuits 25 and 26. The controller 27 includes a memory (not shown) for memorizing a position which is designated by a light pen 13 as will be described. Control means comprise the controller 27, the modulation signal generating circuits 25 and 26, and the drivers 23 and 24.

Reference numeral 4 denotes a half mirror for composing a laser beam which is projected by the first and the second semiconductor lasers 21 and 22, 6 denotes a beam splitter, 7 denotes a two-dimensional scanner for scanning an eye fundus of an eye-to-be-inspected (hereinafter simply referred to as the "eye") H with a laser beam, which has passed through the beam splitter 6, through a lens system 8, and 9 denotes a light receiving element for receiving a laser beam reflected by the eye fundus through the lens system 8, the two-dimensional scanner 7 and the beam splitter 6. The light receiving element 9 outputs light receiving signals corresponding to the light quantity of the visible light and infrared light.

Reference numeral 10 denotes an amplifier for amplifying a light receiving signal which is output by the light receiving element 9, 11 denotes a display for forming an eye fundus image on a display screen 11a by means of electronic beam scanning according to the light receiving signal which is output by the light receiving element 9, and 12 denotes a synchronous control circuit for forming a proper eye fundus image on the display screen 11a by synchronizing the scanning of the two-dimensional scanner 7 and the electronic beam scanning on the display screen 11a. Reference numeral 13 denotes a light pen for designating a desired position on the display screen 11a and irradiating a visible laser beam to a position on the eye fundus corresponding to the designated position and stimulating the designated position. The light pen 13 designates the position by abutting its tip portion against the display screen 11a and when the electronic beam scanning on the display screen 11a scans the designated position, it outputs a timing signal.

Figure 3:
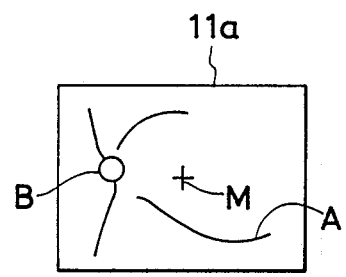
FIG. 3 is a schematic view of an eye fundus image.

If an infrared laser beam is emitted by the second laser beam light source 22 after the alignment of the eye is verified, the infrared laser beam emitted by the second laser beam light source 22 is reflected by the half mirror 4 and made incident upon the two-dimensional scanner 7 through the beam splitter 6. The two-dimensional scanner 7 scans the eye fundus H of the eye E with an infrared laser beam through the lens system 8. The laser beam reflected by the eye fundus is received by the light receiving element 9 through the lens system 8, the two-dimensional scanner 7 and the beam splitter 6. And, a light receiving signal corresponding to the light receiving quantity is output by the light receiving element 9 and input into the display 11 through the amplifier 10. And, an eye fundus image is formed on the display screen 11a as shown in FIG. 3. This eye fundus image formed on the display screen 11a is subjected to observation. In FIG. 3, reference character A denotes a blood vessel and B denotes a papilla.

On the other hand, since the modulation signal generating circuit 25 outputs modulation signals for a predetermined period of time, the driver 23 is activated for the predetermined period of time to drive the first semiconductor laser 21. And, a visible laser beam is emitted by the first semiconductor laser 21 for the aforementioned period time. As a result, a fixation mark M is formed at a predetermined position on eye fundus H and at a position on the display screen 11a corresponding to the predetermined position as shown in FIG. 3.

In the event a view field is inspected, the tip portion of the light pen 13 is abutted against a desired position on the eye fundus image which is formed on the display screen 11a. As a result, a timing signal is output by the light pen 13 at the time point when the electronic beam for scanning the display screen 11a scans the designated position. The controller 27, when the timing signal is input therein, memorizes the designated position according to the timing signal in a memory (now shown).

Figure 4:
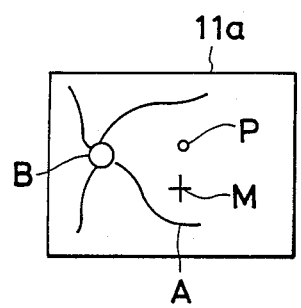
FIGS. 4 and 5 are schematic views of a display screen.

By the way, the controller 27 outputs a second modulation command signal when the laser beam scans the position on eye fundus H corresponding to the designated position which is memorized in the memory. Therefore, when the second modulation command signal is output by the controller 27, a second modulation signal is output by the modulation signal generating circuit 26 either to intensify or decrease the light quantity of an infrared laser beam which is output by the semiconductor laser 22 and the position P is displayed on the display screen 11a as shown in FIG. 4. By this, it is known whether the position, which was designated by the light pen 13, is correctly input into the controller 27 and the position stimulated by a visible laser beam can be confirmed.

Figure 5:
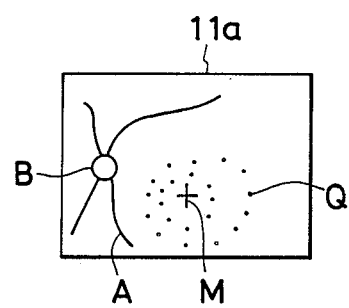

Reference numeral 32 denotes an irritating or stimulating switch. When this stimulating switch 32 is turned on, the controller 27 outputs a first modulation command signal. When the first modulation command signal is output, a first modulation signal is output by the modulation signal generating circuit 25, and then a visible laser beam is emitted by the semiconductor laser 21. The visible laser beam emitted by the semiconductor laser 21 is projected to a position on eye fundus H corresponding to a position designated by the light pen 13 to stimulate that part of the eye fundus. Reference numeral 33 denotes a response switch which is actuated or turned on when the person-to-be-inspected feels the irritation or stimulation. When the response switch 33 is actuated or turned on, a spot Q showing the stimulating position felt is displayed on the display screen 11a as shown in FIG. 5.

When the instrument is used as a subjective optometer by forming a target image such as a landolt ring on the eye fundus, a modulation signal for forming a landolt ring is output by the modulation signal generating circuit 25 in order to control the first semiconductor laser 21 as such that the emission of the laser beam is stopped for the scanning period of time at the position of the eye fundus where the landolt ring is formed and the landolt ring is formed at a desired position on the eye fundus in the same manner as the prior art. In this case, since the infrared laser beam also scans the landolt rang forming position, the alignment of the landolt ring is easy. Moreover, the eye fundus can be observed at the landolt forming position.

Reference numeral 34 denotes an adjusting knob for adjusting the brightness of the background when the landolt ring, etc. are formed on eye fundus H. When the adjusting knob 34 is adjusted, the controller 27 outputs a first modulation command signal for adjusting the light quantity of a visible laser beam which is emitted by the first semiconductor laser 21 so that the background is adequately adjusted in brightness according to the adjustment. The controller 27 composes the visible laser beam and the infrared laser beam with reference to various parameters (these are input as data beforehand) such as sensitivity of the light receiving element 9, reflectance at the eye fundus H with respect to each wavelength of the laser beam, etc. so that the adequately adjusted background brightness can be obtained and calculates the light quantity of the infrared beam for obtaining a proper light receiving signal from the light receiving element 9 when eye fundus H is scanned by the composed beam of light. And, the controller 27 outputs a second modulation command signal required for causing the second semiconductor laser 22 to emit the calculated quantity of an infrared beam. Therefore, even if the visible laser beam is changed in light quantity, an eye fundus image of a constant brightness can always be displayed on the display screen 11a.

If within the range where a proper light receiving signal can be received from the light receiving element 9, the controller 27 may output a second modulation command signal for changing the light quantity of the infrared laser beam at each part of eye fundus H.

By the way, the light quantity of the infrared laser beam during the scanning has three patterns plus a combination of these patterns depending on the light quantity required for various kinds of inspection. The three patterns are; (1) constant, (2) to change in phase with a visible laser beam and (3) to change in opposite phase with a visible laser beam. For example, in the case the visible light quantity is less than the light quantity required for observation, the pattern (2), i.e., to change in phase with a visible laser beam, is selected and this is emphasized on a monitor when a projection pattern is observed.

When the visible light level is sufficient but a pattern portion not illuminated is large, the pattern (3), i.e., to change in opposite phase with a visible laser beam, or the pattern (1), i.e., constant, is used in order to observe the large portion.

In the above embodiment, the designation of the stimulating position, the operation of the stimulation switch, etc. are manually performed. However, they may be operated by a software of the controller 27.

In this way, according to a laser beam scanning type ophthalmological instrument of the present invention, the shortage of light quantity of a visible light for scanning an eye fundus is made up for by an infrared laser beam. Therefore, a partial saturation or a shortage of light quantity do not occur and a satisfactory image can always be obtained. Moreover, even if the infrared light is intensified with respect to an eye-to-be-inspected having an eye fundus of a low reflectance, the person-to-be-inspected does not suffer from a dazzling feeling and thus the eye fundus can be observed without any trouble. Therefore, since the amplification factor of the amplifier system is not required to be increased, there does not occur a case where a correct observation of the eye fundus is difficult to obtain because of increase of noise of the amplifier system. Furthermore, the ophthalmological instrument according to the present invention can also be used as a laser coagulator by intensifying the light quantity of a visible laser beam.

Figure 6:
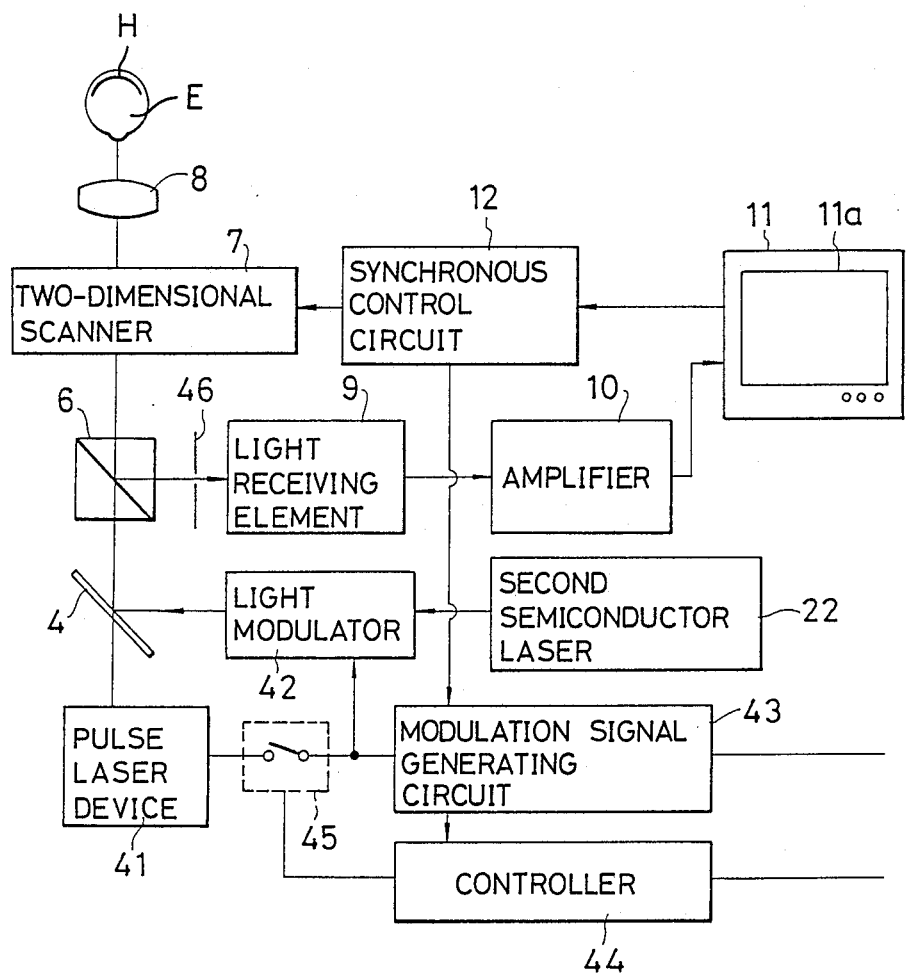
FIG. 6 is a schematic view of a second embodiment of the present invention.

FIG. 6 illustrates one example in which the present invention is applied to a laser beam coagulator. In the figure, reference numeral 41 denotes a pulse laser device for emitting a pulse laser beam for coagulating a predetermined place of an eye fundus, and reference numeral 42 denotes a light modulator for adjusting the light quantity of an infrared laser beam output by the semiconductor laser 22. The light modulator 42 usually permits an infrared light of a certain intensity to pass. The light modulator 42 also increases or decreases the quantity of the light which is permitted to pass according to a modulation signal which is output by the modulation signal generating circuit 43.

Reference numeral 44 denotes a controller. The controller 44 opens and closes a logic gate and outputs a modulation signal from the modulation signal generating circuit 43. The controller 44 closes the logic gate 45 upon actuation of the start switch and projects a pulse laser beam to an eye fundus position corresponding to a position on the display screen 11a designated by the light pen 13. Reference numeral 46 denotes a filter (preventing means) for preventing the light receiving element 9 from being broken by an intensified reflecting light of the pulse laser beam and for preventing the amplifier 10 from being saturated. Instead of the filter 46, there maya be used a wavelength split mirror, a shutter, an acoustic optical element or the like.

In the above-mentioned instrument, the point designated by the light pen 13 for performing the coagulation and the eye fundus image are displayed in an overlapped state. Furthermore, a pointed place can be coagulated at one time by designating a plurality of points and by designating the point in dimension or area. In any of the above embodiments, the light pen 13 is utilized as a tool for designating a desired position on the display screen 11a. However, the tool for designating a desired position is not limited to this. For example, a joy stick or the like may be used for it.

As described in the foregoing, according to the present invention, no partial saturation nor shortage of light quantity are occurred, and always a satisfactory image can be obtained. Even when the reflectance of an eye fundus is low, an image of the eye fundus can be observed without increasing the noises of an amplifier system because a second laser beam used for observing the eye fundus may simply be intensified without increasing the amplification factor of the amplifier system. Furthermore, even in the case a landolt ring, etc. are formed on the eye fundus by a first laser beam, since a second laser beam also scans the landolt ring forming position, the eye fundus at the position where the landolt ring is formed can be observed. Moreover, the alignment of the landolt ring, etc. becomes comparatively easy. In addition, since the actual stimulating position is confirmed through a two-dimensional scanning portion, more correct confirmation can be obtained. Thus, no positional displacement occurs.

What is claimed is:

1. A laser beam scanning type ophthalmological instrument for observing and testing an eye fundus, comprising:
    a first laser beam light source for emitting a first laser beam;
    a second laser beam light source for emitting a second laser beam of a different wavelength from that of said first laser beam;
    a light receiving element for receiving light reflected by an eye fundus;
    means for scanning the eye fundus with said first and second laser beam; and
    means for forming an image in response to light from both said first laser beam light source and said second laser beam light source reflected from the eye fundus,
    said first and second laser beams emitted by said first and second laser beam light sources can independently be adjusted in light quantity.

2. A laser beam scanning type ophthalmological instrument according to claim 1, which further includes control means for establishing light quantity of the other laser beam when a target value of output power from said light receiving element and light quantity of either one of said first and second laser beams are established.

3. A laser beam scanning type ophthalmological instrument according to claim 2, wherein said control means adjusts the light quantity of said first and second laser beam with reference to reflectance at the eye fundus with respect to a wavelength which is input as data beforehand and wavelength characteristic of said light receiving element, so that the output power of said light receiving element becomes constant.

4. A laser beam scanning type ophthalmological instrument comprising:
    a first laser beam light source for emitting a first laser beam;

a second laser beam light source for emitting a second laser beam of a different wavelength from that of said first laser beam;

a light receiving element for receiving light reflected from the eye fundus;

a display for displaying an image of the eye fundus thereon when said light receiving element has received the reflected laser beam scanning means for scanning the eye fundus with said first and second laser beams, one of said first and second laser beams is used for selectively stimulating or coagulating a portion of the eye fundus control means for separately controlling light quantity of said first and second laser beams emitted by said first and second laser beam light sources and for controlling said display; and designating means for designating a desired position on the eye fundus, said control means causing said display means to display an image of the portion of the eye fundus corresponding to the designated position on said display in accordance with modulation of either one of said first and second laser beams.

5. A laser beam scanning type ophthalmological instrument according to claim 4, wherein one of said first and second laser beams is modulated.

6. A laser beam scanning type ophthalmological instrument according to claim 5, wherein one of said laser beams for observation has a wavelength outside of the visible spectrum.

7. A laser beam scanning type ophthalmological instrument according to any one of claims 4 through 6, which further includes preventing means for preventing reflected light of either one of said first and second laser beams from being made incident to said light receiving element while the laser beam is used for coagulation.

8. A laser beam scanning type ophthalmological instrument according to claim 7, wherein said preventing means includes a wavelength split mirror or a filter.

9. A laser beam scanning type ophthalmological instrument according to claim 7, wherein said preventing means includes an acoustic optical element.

10. A laser beam scanning type ophthalmological instrument according to claim 7, wherein said preventing means includes a shutter.

11. A laser beam scanning type ophthalmological instrument according to claim 4, wherein when said designating means designates a plurality of positions, the plurality of positions are substantially simultaneously subjected to coagulation.

* * * * *